(12) United States Patent
Kordyum et al.

(10) Patent No.: US 6,268,178 B1
(45) Date of Patent: Jul. 31, 2001

(54) PHAGE-DEPENDENT SUPER-PRODUCTION OF BIOLOGICALLY ACTIVE PROTEIN AND PEPTIDES

(75) Inventors: Vitaliy A. Kordyum; Svetlana I. Chernykh; Irina Y. Slavchenko; Oleksandr F. Vozianov, all of Kiev (UA)

(73) Assignee: Phage Biotechnology Corp., Irvine, CA (US)

(*) Notice: Subject to any disclaimer, the term of this patent is extended or adjusted under 35 U.S.C. 154(b) by 0 days.

(21) Appl. No.: 09/318,288

(22) Filed: May 25, 1999

(51) Int. Cl.$^7$ ............... C12P 21/00; C12N 7/00; C12N 1/21; C12N 15/70; C07H 21/04

(52) U.S. Cl. ............... 435/69.1; 435/69.51; 435/320.1; 435/252.3; 435/471; 435/235.1; 536/23.1

(58) Field of Search ............... 435/69.1, 252.3, 435/69.4, 69.51, 243, 320.1, 235.1, 471; 536/23.1

(56) References Cited

U.S. PATENT DOCUMENTS

| | | | |
|---|---|---|---|
| 4,637,980 | * 1/1987 | Auerbach et al. | ............... 435/68 |
| 4,710,463 | 12/1987 | Murray . | |
| 4,716,112 | 12/1987 | Panayotatos . | |
| 4,775,622 | 10/1988 | Hitzeman et al. . | |
| 5,102,797 | 4/1992 | Tucker et al. . | |
| 5,196,318 | 3/1993 | Baldwin et al. . | |
| 5,346,830 | 9/1994 | Christie . | |
| 5,641,673 | 6/1997 | Haseloff et al. . | |
| 5,646,013 | 7/1997 | Takano et al. . | |
| 5,834,209 | 11/1998 | Korsmeyer . | |
| 5,834,233 | 11/1998 | Molin et al. . | |
| 5,861,273 | 1/1999 | Olson et al. . | |

FOREIGN PATENT DOCUMENTS

| | | |
|---|---|---|
| 0 140 864 | 5/1985 | (EP) . |
| 0043980 | 9/1987 | (EP) . |
| 0 372 707 | 6/1990 | (EP) . |
| 2130222A | 5/1984 | (GB) . |
| 2143238A | 2/1986 | (GB) . |

OTHER PUBLICATIONS

Friedman, David and Gottesman, Max. Lytic mode of Lambda development. In Lambda II. Roger Hendrix, ed. pp21–51, Cold Spring Harbor Laboratory Press, 1983.*

Henthorn, et al. Journal of Molecular Biology 257: 9–20, 1996.*

Berendson, et al. Science 282: 642–643, 1998.*

Chen, et al. "Temperature Induction of Bacteriophase λ mutants in *Escherichia coli*." *Journal of Biotechnology*. 1995. pp. 87–97.

N.E. Murray et al., "Manipulation of restriction targets in phage λ to form receptor chromosomes for DNA fragments", Nature 251, pp. 476–481, 1974.

B. Fischer et al., "Isolation, Renaturation, and formation of disulfide bonds of eukaryotic proteins expressed in *escherichia coli* as inclusioin bodies", P. Biotech and Bioenginerring, pp. 41:3–13, 1993.

T. Mantiatis et al., "Molecular Cloning: A Laboratory Manual", 1982, Cold Spring Harbor Laboratory Press, pp. 17–27.

A. Moir et al., "The use of specialised transducing phages in the amplification of enzyme production", Molec. Gen. Genet., 149, pp. 87–99, 1976.

S.M. Panasenko et al., "Five–Hundredfold overproduction of DNA ligase after induction of a hybrid lambda lysogen constructed in vitro", Science, 196, pp. 188–189, 1977.

N.E. Murray et al., "Characterization of λpolA transducing phages; effective expression of the *E. coli polA*", Molec. Gen. Genet, 175, pp. 77–87, 1979.

S. M. Chaykovakaya, English Abstract Only, Antibiotics 7(5): 453–456, 1962.

J.H. Miller, Experiments in Molecular Genetics, Cold Spring Harbor Laboratory Press, 1972, Experiment 57, 60 and 62.

Koh et al., "Vectors lambda 200g and lambda 200c: two useful derivatives of lambda 2001", Gene 130, pp. 117–119, 1993.

* cited by examiner

*Primary Examiner*—David Guzo
*Assistant Examiner*—Gerald G. Leffers, Jr.
(74) *Attorney, Agent, or Firm*—Knobbe, Martens, Olson & Bear, LLP

(57) ABSTRACT

This invention relates to a method for enhancing the production of biologically active proteins and peptides in bacterial cells by infecting bacterial cells of the producer strain, which contain a plasmid with one or more targeted genes, with bacteriophage λ with or without the targeted gene(s). The phage increases synthesis of the targeted protein and induces lysis of the producer strain cells. Super-production is achieved by cultivating the producer strain cells under culture conditions that delay lytic development of the phage. The biologically active proteins and peptides subsequently accumulate in a soluble form in the culture medium as the cells of the producer strain are lysed by the phage.

16 Claims, No Drawings

PHAGE-DEPENDENT SUPER-PRODUCTION OF BIOLOGICALLY ACTIVE PROTEIN AND PEPTIDES

BACKGROUND OF THE INVENTION

1. Field of the Invention

This invention relates to recombinant DNA technology and more particularly to a new method for enhancing the production of heterologous proteins in bacterial host cells. The disclosed method involves infecting host cells, which contain plasmid encoding the gene of interest, with bacteriophage λ to induce lysis of the bacterial host cells. Super-production may be achieved in selected host cells either when the plasmid alone carries at least one copy of the heterologous DNA or when both plasmid and phage λ each carry at least one copy of the heterologous DNA.

2. Description of the Related Art

At present, genetic engineering methods allow creating microorganism strains capable of producing substantial amounts of various bioactive substances having important applications in medicine and industry. Typically, plasmid vectors into which a heterologous gene has been inserted are used to transform bacterial host cells. Different strains of *E. coli* are frequently used as recipient cells. Using such plasmid-dependent transformation methods, *E. coli* cells have been engineered to produce a variety of valuable human peptides and proteins, including insulin, γ-interferon, a number of interleukins, superoxidedismutase, plasminogen activator, tumor necrosis factor, erythropoietin, etc. These substances are either already used in medical practice or undergoing different stages of clinical studies.

However, the plasmid method has serious disadvantages. It is technologically complicated, since the desired product has to be extracted from bacterial cells after biosynthesis, which is a multi-stage process. For example, interferon extraction involves disintegration of cells, buffer extraction, polyethylene-imine processing, clarification, precipitation by ammonium sulfate, dialysis, and centrifugation (Goeddel, EP 0043980). The necessity for such extraction and purification steps not only complicates production technology of the recombinant product, but also results in substantial losses, especially during large-scale industrial production.

A further complicating factor is that at relatively high levels of expression of the cloned genes, the eukaryotic proteins generated tend to accumulate in the cytoplasm of *E. coli* as insoluble aggregates, which are often associated with cell membranes. Consequently, the already difficult extraction and purification methods discussed above must be supplemented with additional technical procedures related to the extraction of the insoluble inclusion bodies. Usually, the insoluble proteins are solubilized using ionic detergents, such as SDS or laurylsarcosine, at increased temperatures or in the presence of denaturants, such as 8 M urea or 6–8 M guanidine-HCl.

Often, the final stage of purification involves renaturation and reoxidation of the solubilized polypeptides, which is required to restore functional activity. Disulfide bonds, which are necessary for proper folding of the protein in its native conformation, must be reformed. Renaturation procedures, such as disulfide interchange, may use expensive and relatively toxic reagents, like glutathione, and oxidized 2-mercaptoethanol or dithiothreitol. Further, the final yield of bioactive genetically-engineered proteins may be relatively low. Moreover, the presence of even trace concentrations of the toxic reagents needed to solubilize and then re-establish secondary and tertiary protein structure may prohibit subsequent clinical application of the proteins. Thus, the generation of targeted protein in the form of insoluble inclusion bodies within the bacterial host cells not only complicates the production of recombinant proteins and results in diminished yield, but may also render the final protein unsuitable for clinical use (Fisher, B., Summer, I., Goodenough, P. Biotech. and Bioeng. 41:3–13, 1993).

The technological difficulties associated with the extraction of proteins produced by the expression of heterologous genes from plasmid-transformed bacterial host cells may be overcome by infecting the transformed bacterial host cells with bacteriophage, whose lytic pathway results in lysis of the bearer cell. Thus, the desired protein may be simply released into the culture medium (Breeze A. S. GB 2 143 238A). Accordingly, Breeze disclosed a method of increasing the yield of enzyme produced in *E. coli* by infecting the bacterial cells with phage λ carrying a temperature-sensitive mutation in cI to provide controlled lysis. The cI-gene product is a repressor of early transcription and consequently blocks transcription of the late region of the phage DNA, which is required for head and tail assembly and cell lysis (Mantiatis, T., Fritsch, E. F., Sambrook, J., MOLECULAR CLONING: A LABORATORY MANUAL, 1982, Cold Spring Harbor Laboratory Press). Bacteriophages carrying a temperature-sensitive mutation in cI are able to establish and maintain the lysogenic state as long as the cells are propagated at a temperature that allows the cI-gene product to repress transcription of phage genes necessary for lytic growth. Accordingly, the transformed bacterial host cells may be cultivated at 30° C., wherein the cI-mediated suppression of phage DNA transcription continues and the phage remains in the lysogenic state, until the stage of maximum ferment production is reached. Subsequently, the culture temperature may be increased to 42° C. for 30 minutes in order to inactivate the cI repressor and permit the phage to begin its lytic development. The host cells may then be incubated for 2–3 hours at 30° C. to allow complete lysis and release of the enzyme (Breeze A. S. GB 2 143 238A).

Although Breeze teaches release of proteins from bacterial producer cells, it requires cultivating producers at temperatures not exceeding 30° C., which is not the optimum temperature for growth of *E. coli* cells. Synthesis at the optimum temperature (37° C.) is not possible, since cells at temperatures exceeding 32° C. undergo lysis before reaching the stage of maximum ferment accumulation due to the development of temperature-sensitive lytic prophage. Furthermore, incubation of the bacterial host cells at 42° C. for 30 min as disclosed by Breeze may activate proteases that destroy the targeted protein.

Auerbach et al. (U.S. Pat. No. 4,637,980) used a phage λ DNA fragment for inducing lytic release of recombinant products. In that method, like Breeze, the temperature-sensitive mutation in λ cI-gene product was used to provide temperature-dependent lysis of the bacterial host cells. The λ DNA fragment in Auerbach maintained functional endolysin-encoding genes, N, Q, R and S, for producing lysozyme following inactivation of the cI repressor at 42° C. Most of the remaining phage genes were deleted; mutations in O and P genes prevented replication of the phage DNA. Consequently, the λ DNA was not a fully functional phage, capable of modulating expression of the targeted gene. Moreover, the λ DNA of Auerbach was not suitable for use as a vector for carrying targeted genes. Further, as discussed above, incubation of the bacterial host cells at 42° to 44° C. for 90–120 min as disclosed by Auerbach may activate proteases that destroy the targeted protein.

In addition to providing for the lytic release of intact protein from bacterial producer cells, bacteriophages have also been used as an alternative to bacterial plasmid-based vectors, for carrying heterologous DNA into host bacterial cells. (Murray, N. E. and Murray, K., Nature 251:476–481, 1974; Moir, A., Brammar, W. J., Molec. gen. Genet. 149:87–99, 1976). Typically, amplification of genes and their products is achieved during lytic growth of the phage, wherein the phage genome is integrated into the bacterial host DNA (Panasenko, S. M., Cameron, J. R., Davis, R. V., Lehman, L. R., Science 196:188–189, 1977; Murray, N. E. and Kelley, W. S., Molec. gen. Genet. 175:77–87, 1979; Walter, F., Siegel, M., Malke, H., 1990, DD 276,694; Mory, Y., Revel, M., Chen, L., Sheldon, I. F., Yuti-Chernajovsky, 1983, GB 2,103,222A). Usually, either lysogenic cultures of recombinant phage λ are used for infecting the bacterial host cells, or "warmed up" bacterial cultures, already harboring recombinant lysogenic phage λ, are grown up to amplify expression of the heterologous genes.

Although there are examples of the successful use of λ vectors for expression of heterologous genes, λ vectors have been used primarily for gene cloning. Once cloned, the genes are transferred to plasmid vectors for more effective expression. For example, when E. coli is infected by phage λ Charon 4A C15, containing the human β-interferon gene, the quantity of interferon in cell lysate constituted $7-8\times10^6$ units/liter. After the DNA fragment bearing targeted gene was recloned from phage to plasmid, β-interferon yield increased to $1\times10^8$ units/liter (Moir, A., Brammar, W. J., Molec. gen. Genet. 149:87–99, 1976).

To increase the yield of heterologous protein generated in bacterial host cells by recombinant λ vectors, mutations in the phage genome have been introduced that cause phage λ to lose its ability to initiate bacterial cell lysis. Enhanced yield is thereby achieved by extending the period of time during which the heterologous gene is expressed by the bacterial host cells. Thus, for example, the yield of DNA ligase 1 in lysogenic cultures containing λ gt4ligS prophage, with amber-mutation in the S gene, was five times greater than the yield of DNA ligase 1 in lysogenic cultures containing λ gt4lig prophage without the amber-mutation (Panasenko, S. M., Cameron, J. R., Davis, R. V., Lehman, L. R., Science 196:188–189, 1977). The phage λ S protein is required for lysis; therefore S⁻ mutants accumulate large numbers of intracellular progeny phage particles, as well as the targeted protein, without lysing the host cells (Mantiatis, T., Fritsch, E. F., Sambrook, J., MOLECULAR CLONING: A LABORATORY MANUAL, 1982, Cold Spring Harbor Laboratory Press).

Similar increases in the yield of DNA polymerase 1 were reported for lysogenic cultures containing recombinant phage λ with amber-mutations in the S and Q genes, compared to recombinant phage λ without the amber-mutations (Murray, N. E. and Kelley, W. S., Molec. gen. Genet. 175:77–87, 1979). The phage λ Q protein is required for transcription of the late region of the phage DNA, which includes many genes involved in head and tail assembly and cell lysis. (Mantiatis, T., Fritsch, E. F., Sambrook, J., MOLECULAR CLONING: A LABORATORY MANUAL, 1982, Cold Spring Harbor Laboratory Press).

In U.S. Pat. No. 4,710,463, Murray discloses lysogenizing a non-suppressing (Su°) strain of E. coli with phage λ containing the temperature-sensitive mutation in cI, as well as mutations in λ S and E genes. Consequently, prolonged cultivation of the lysogenic E. coli at 37° C. leads to high levels of production of the recombinant protein, which is retained within the cells, since these are not lysed by phage gene products in the normal way, and since the recombinant phage genome is not encapisdated, it remains available for transcription.

Despite the enhanced yield of heterologous proteins possible using λ-vectors with S and E mutations, the potential technical advantages of bacteriophage vectors related to the lytic release of targeted proteins, may be lost with these mutations, because the targeted proteins accumulate inside the bacterial cell. Thus, when a lysis-defective mutant λ-vector is used for production of heterologous protein, the extraction and purification steps, discussed above for bacterial cells transformed by plasmid vectors, along with the resultant losses, must be performed.

SUMMARY OF THE INVENTION

The present invention discloses a method for producing a biologically active protein of interest. The method comprises the steps of: (1) transforming a bacterial host cell with a plasmid having at least one copy of an expressible gene encoding the protein, (2) infecting the transformed bacterial host cell with a bacteriophage capable of mediating lysis and also capable of lytic growth without lysis, and (3) cultivating the bacterial host cell under a culture condition that induces lytic growth of the cell without lysis until a desired level of production of the protein is reached.

In a preferred embodiment, the bacteriophage has a temperature-sensitive mutation. More preferably, the bacteriophage is bacteriophage λ and the temperature-sensitive mutation is $cI_{857}$. The culture condition that induces lytic growth of the bacteriophage is at a temperature of greater than 32° C. Prior to the cultivating step, the bacterial host cells may be grown at a temperature, generally less than about 32° C. that prevents lytic growth of the bacteriophage.

In a variation of the disclosed method, the bacteriophage has a mutation in at least one gene involved in bacteriophage-mediated lysis of the bacterial host cell.

Preferably, the bacteriophage is bacteriophage λ and the at least one gene involved in bacteriophage-mediated lysis is selected from the group consisting of N, Q and R.

Moreover, the bacterial host cell is preferably from a strain of E. coli. The strain of E. coli may or may not produce a suppressor for the repair of amber-mutations.

Bacteriophage-mediated lysis of the bacterial host cell may be delayed by culturing at higher multiplicities of infection compared to lower multiplicities of infection. The infecting bacteriophage may be provided at a multiplicity of infection in a range of about 1 to about 100 and more preferably, at a multiplicity of infection in a range of about 10 to about 25.

In another aspect of the present invention, the bacteriophage may contain at least one copy of an expressible gene encoding the same heterologous protein which is encoded by the plasmid.

A variation of the method for producing a biologically active protein in accordance with the present invention is disclosed. The method comprises the steps of: (1) transforming a bacterial host cell with a plasmid having at least one copy of an expressible gene encoding the protein, (2) infecting the transformed bacterial host cell with a bacteriophage having at least one copy of an expressible gene encoding the protein, and (3) cultivating the bacterial host cell under a culture condition that allows expression of the plasmid and phage genes.

In accordance with another aspect of the present invention, a bacterial host cell is disclosed. The bacterial host cell has a plasmid with at least one copy of an expressible heterologous gene encoding a protein, wherein the host cell is infected with a bacteriophage capable of mediating lysis and also capable of lytic growth without lysis.

The bacterial host cell preferably has a bacteriophage with a temperature-sensitive mutation. More preferably, the bacterial host cell is infected with bacteriophage λ and the temperature-sensitive mutation is $cI_{857}$.

In a variation of the bacterial host cell, the bacteriophage has a mutation in at least one gene involved in bacteriophage-mediated lysis of the host cell. Preferably, the bacterial host cell is infected with bacteriophage λ having a mutation in at least one gene selected from the group consisting of N, Q and R. More preferably, the bacterial host cell is infected with bacteriophage λ with $cI_{857}$, $Q_{am\ 117}$ and $R_{am\ 54}$ mutations.

In a preferred embodiment of the bacterial host cell of the present invention, the host cell has a plasmid encoding a protein of interest and is also infected with a bacteriophage having at least one copy of an expressible gene encoding the protein of interest.

The bacterial host cell in accordance with the present invention is preferably a strain of E. coli. The strain of E. coli may or may not have a suppressor for repairing amber-mutations. Similarly, the strain of E. coli may or may not be recA deficient. One preferred strain of E. coli host cells in accordance with the present invention contains a plasmid having at least one copy of an expressible heterologous gene encoding a protein, wherein the strain of E. coli is infected with bacteriophage λ having $cI_{857}$, $Q_{am\ 117}$ and $R_{am\ 54}$ mutations. The protein may be human alpha-2b interferon. More preferably, in addition to having a plasmid with at least one copy of a gene encoding a protein, the E. coli host cell also has a bacteriophage λ having $cI_{857}$, $Q_{am\ 117}$ and $R_{am\ 54}$ mutations and at least one copy of a gene encoding the protein. This bacteriophage preferably lacks a suppressor for repairing amber-mutations.

DETAILED DESCRIPTION OF THE PREFERRED EMBODIMENT

Bacteriophage λ is useful as a vector because more than 40% of the viral genome is not essential for lytic growth. This area of the λ genome, located in the central region of the λ DNA, between genes J and N, may be replaced by heterologous DNA encoding a desired product. That region is transcribed early during infection.

In order to maximize the expression of a targeted gene, whose synthesis information is recorded in the area of phage's early genes, special conditions for the phage's development must be provided to ensure proper replication. Further, transcription of the early area, containing the targeted gene, should be fostered, while transcription of the later genes, involved in cell lysis, should be decelerated. This slows down maturation of the λ particles and subsequent cell lysis. Consequently, the early phage products, including the targeted gene product, will accumulate in the bacterial cells. Deceleration of late transcription, thereby extending expression of the targeted gene, may be accomplished by: (1) mutations of phage genome that block expression of the later genes (2) increased multiplicity of infection, and/or (3) cultivation of the infected bacterial cells at a reduced temperature.

An important advantage of infecting producer cells with a bacteriophage is that the phage causes a profound rearrangement of all macromolecular synthesis in the bacterial host cells. By turning off transcription of bacterial genes, phages may increase the copying of the targeted gene, and consequently, increase the output of desired product.

In a preferred embodiment of the present superproduction system, phage λ with amber-mutations that delay bacterial lysis (e.g., $Q^-$ and $R^-$ mutations) are provided in a strain of E. coli, designated Su°, which lacks the suppressor responsible for correcting amber-mutations in phage λ. In order to obtain a non-suppressing (Su°) strain of E. coli, Su° clones are selected from the wild-type Su⁺ population. Preferably, a selection marker is inserted into the phage DNA, e.g., tetracycline or ampicillin resistance.

Selection of Bacterial Strains

Selection of non-suppressing (Su°) strains of E. coli, for example, E. coli K 802 was carried out with phage λ $cI_{857}$ Nam7Nam53 bla tet (hereinafter λ bla N'). Strain E. coli C600 (λ bla N') served as source of the phage. This phage was obtained by insertion of plasmid pCV 11 (bla tet) at EcoRI site into single-site (EcoRI) vector carrying ts-mutation in repressor gene ($cI_{857}$). Then two amber-mutations were introduced into the phage N gene by recombination in vivo.

Clones were tested for non-lysogenicity with phage λ clear. In addition to phage λ bla N', phage λ $cI_{857}$ $Q_{am117}$ $R_{am\ 54}$ was used to check for suppressor.

Media—Liquid nutrient media, LB and M9 as well as agar medium LB were used for bacterial culture growth (Miller J. H., 1972, Experiments in molecular genetics, Spring Cold Harbor, N.Y.).

Preparation of Phage Lysate—Lysogenic culture was grown in broth at 28° C. under intense aeration to a density of $2 \times 10^8$ cells/ml followed by incubation at 43° C. for 20 min. Then it was kept at 37° C. under intense aeration. Cells were lysed in 60–80 min and phage was released into the cultural medium. Phage titer was estimated by a conventional two-layer technique. As a rule, $2 \times 10^{10}$ PFU/ml of phage lysate were obtained.

As is known, phage λ N' mutant is not able to lyse the host cells and is present in cells in the form of extremely unstable plasmids. If the host cells contain suppressor, the amber-mutation is phenotypically corrected, the N protein is synthesized and the phage can develop lytically. This difference in the viability of Su$^+$ and Su$^°$ cells, infected by λ N', is used as a basis for selection of spontaneously appearing Su$^°$ revertants from the E. coli Su$^+$ cell population. Phage λ with an inserted plasmid that introduced the ampicillin and tetracycline resistance markers into cells was used to prevent the nonlysing Su$^°$ cells from masking the search for mutants. The phage also contains ts-mutation in the repressor gene that permits lytic development of such phage resulting in cell lysis.

If the medium supplemented with ampicillin and tetracycline is inoculated with Su$^+$ culture after its infection with phage λ bla N' with subsequent growth at 43° C., single suppressor-free cells containing phage λ bla N' in the form of plasmids must develop on plates. Su$^°$ derivatives of the parent cultures are obtained by curing the cells from the phage. The method can be subdivided into several stages.

1. Infection of Culture With Phage λ bla N'

The culture E. coli Su$^+$ was grown on the M9 medium with maltose at 37° C. under intense agitation to a density of 1–2×10$^8$ cells/ml. The cells were infected with phage λ bla N' at a multiplicity of 5–10 particles per cell and incubated for 20 min at 20° C. Under given conditions, the infection efficiency is about 100%, in addition to the bulk of Su$^+$ cells, the phage also infects single Su$^°$ cells.

2. Selection of Suppressor-Free Cells Containing Marker Phage

After infection, cells were plated out on agar medium supplemented with 12 γ/ml tetracycline and 20 γ/ml ampicillin and grown at 43° C. In 24 h, single colonies developed, which were replated on agar medium with antibiotics and grown at 37° C.

3. Curing of the Selected Clones From Phage λ bla N'

Since phage λ N' in the E. coli Su$^°$ cells is in the form of extremely unstable plasmids, in order to cure from the phage the selected clones were plated on selective agar medium without antibiotics and grown at 37° C. The number of cells that had lost the phage in the first passage on the medium without antibiotics amounted to 12–35%. The selection of such cells was carried out by monitoring the loss of antibiotic resistance and the acquisition of sensitivity to phage λ clear.

4. Testing of Cells for Repressor

The ability of phage λ with amber-mutations to form plaques on lawns of cured clones was checked. Isogenic suppressor-free derivatives of the parent E. coli Su$^+$ strains are clones, on which phage λ bla N' did not form plaques, phage λ cI$_{857}$ Q$_{am117}$ R$_{am54}$ produced 1–3×10$^{10}$ PFU/ml, and phage λ cI$_{857}$ without mutations in genes Q and R produced 1×10$^{10}$ PFU/ml.

Using this method, Su$^°$ revertants of E. coli K 802 Su$^+$ were obtained. Based on the cell number at the moment of infection and the number of Su$^°$ revertants among them, the frequency of occurrence of suppressor-free cells was about 3×10$^{-7}$.

The use of suppressing (Su$^+$) and non-suppressing (Su$^°$) host strains together with phage λ to achieve super-production of heterologous proteins and peptides may be more fully understood from the following working examples.

EXAMPLE 1

Increased Synthesis of β-Lactamase in E. coli Transformed with pBR322 Carrving the β-Lactamase Gene (bla) following Infection by Phage λ

Bacterial cells, E. coli C-600 Su$^+$, were transformed with plasmid pBR322-bla and cultivated in Aminopeptid medium (manufactured at the Leningrad meat processing and packing factory), diluted 1:1 in 0.15 M NaCl. The C-600 Su$^+$/pBR322-bla transformants were then grown at 37° C. to a density of 1×10$^8$ cells/ml and divided into three portions. The control portion was left intact. The second portion was infected with phage λ having the temperature-sensitive mutation in cI, designated λ cI$_{857}$, and the third portion was infected with phage λ having the temperature-sensitive mutation in cI, as well as amber-mutations in the Q and R genes, designated λ cI$_{857}$ Q$_{am\ 117}$ R$_{am54}$. Phage mutations were accomplished by standard recombinant method in vivo. Phage multiplicity was approximately 10 phage bodies per 1 bacterial cell. The λ-treated cultures were incubated for 15 min at 37° C. to inactivate the cI repressor, and then for 19 hr at 28° C. The control cultures were incubated at 37° C. for the entire period. β-Lactamase activity was determined by iodometric assay as described by Chaykovakaya, S. M. and Venkina, T. G. Antibiotics 7(5):453–456, 1962. A unit of activity is defined as the minimum quantity of ferment necessary to inactivate 1×10$^{-7}$ M penicillin (60 units) in 1 hr at 37° C., pH 6.8–7.0.

TABLE 1

| | Bacterial Cell Culture | β-Lactamase Activity (Units) |
|---|---|---|
| 1 | C-600 Su$^+$/pBR322-bla | 833 |
| 2 | C-600 Su$^+$/pBR322-bla + λcI$_{857}$ | 4400 |
| 3 | C-600 Su$^+$/pBR322-bla + λcI$_{857}$Q$_{am117}$R$_{am54}$ | 8300 |

As shown in Table 1, β-lactamase synthesis in the C-600 Su$^+$/pBR322-bla cells infected by phage λ with mutations in the later genes, Q and R, is almost 10 times greater than the synthesis in C-600 Su$^+$/pBR322-bla control cells.

EXAMPLE 2

Increased Output of β-Lactamase Encoded by bla-Gene Contained in Both Plasmid and Phage Cultures of E coli W 3101 recA$^-$13 Su$^°$ with and without transformation by pBR322-bla were cultivated in Aminopeptid medium diluted 1:1 with 0.15 M NaCl, at 37° C. to a density of 1×10$^8$ cells/ml. A recA$^-$ strain was used because these cells have a reduced ability to conduct recombination in areas of extended homology in both plasmid and phage (e.g. bla-gene). Thus, recA$^-$ cultures avoid exclusion of the homologous bla-gene. The cultures were divided into two portions. The first portion, which was not exposed to phage, was incubated at 37° C. for 16 hr. The second portion was infected with phage λ cI$_{587}$ bla Q$_{am\ 117}$ R$_{am\ 54}$ at a multiplicity of about 10 phage bodies per 1 bacterial cell and cultivated for 2.5–3 hr at 37° C., and then for an additional 14 hr at 28° C. β-Lactamase activity was measured by the iodometric method. The results, shown in Table 2 (below), are expressed in units, as defined above for Table 1.

Phage λ cI$_{587}$ bla Q$_{am\ 117}$ R$_{am\ 54}$ was prepared from lysogenic cultures maintained at 28° C. in Aminopeptid medium. When the bacterial cell density reached about 1×10$^8$ cells/ml, the cells were warmed for 20 minutes at 43° C. in order to inactivate the cI repressor. Consequently, the prophage is excised from the bacterial genome and begins its lytic development. After 50 min, the cells underwent lysis, releasing 100–200 bodies each. At a density of 1×10$^8$ cells/ml, the cultures produced 1–2×10$^{10}$ phage bodies per ml. Thus, to infect bacterial cells with phage at a multiplicity of about 10 means that 1 ml of phage lysate (1×10$^{10}$ phage bodies) was added to 10 ml of bacterial suspension (1×10$^9$ cells).

TABLE 2

| Bacterial Cell Culture | β-Lactamase Activity (Units) |
| --- | --- |
| 1  W 3101 recA$^-$13 Si°/pBR322-bla | 13,555 |
| 2  W 3101 recA$^-$13 Su° + λcI$_{857}$blaQ$_{am117}$R$_{am54}$ | 227,796 |
| 3  W 3101 recA$^-$13 Su°/pBR322-bla + λcI$_{857}$blaQ$_{am117}$R$_{am54}$ | 2,000,000 |

As shown in Table 2, bacterial cells which were transformed with both plasmid containing the targeted gene and phage carrying the same gene, produced about 10 times more recombinant protein (β-lactamase) than bacterial cells transformed with phage alone, and over 100 times more β-lactamase than bacterial cells transformed by plasmid alone.

EXAMPLE 3

Super-Production of the β-Galactosidase Encoded by lac-Gene Contained in Both Plasmid and Phage Cultures of *E. coli* RLM1 containing prophage λ cI$_{857}$ plac5 Q$_{am\ 117}$ R$_{am\ 54}$ (carrying a copy of the β-galactosidase gene, lac5) were grown in LB medium (Difco) at 30° C. with intensive aeration to a density of approximately 1×10$^8$ cells/ml. The lysogenic culture was warmed to 43° C. and incubated for 20 minutes to inactivate cI repressor. The temperature was then decreased to 37° C. and the bacterial cells underwent lysis, with phages being formed at 1–2×10$^{10}$ PFU/ml. Subsequently, 10 liters of phage lysate, containing about 1×10$^{10}$ phage bodies (λ cI$_{857}$ plac5 Q$_{am\ 117}$ R$_{am\ 54}$) per ml, were added to 40 liters of a suspension of *E coli* Ca 77 Su° transformed by plasmid pZ56 at a density of about 1×10$^8$ cells/ml in LB medium. Thus, the multiplicity of infection was 25, i.e., there were 25 phage bodies per bacterial cell.

After 7 hr at 37° C., recombinant β-galactosidase constituted 1.9 g per liter of culture medium. The activity of β-galactosidase was calculated by the method of Miller (Miller, J. H., EXPERIMENTS IN MOLECULAR GENETICS, 1972, Cold Spring Harbor Laboratory Press). A unit of activity was calculated as the minimum quantity of ferment required to hydrolyze 1 μM ortho-nitrophenyl-β-D-galactoside to ortho-nitrophenol per min at 30° C., pH 7.0.

EXAMPLE 4

Super-Expression of Human Interferon α-2b

Su$^+$ and Su° strains of *E. coli* K 802, transformed with a plasmid bearing a single copy of the gene encoding alpha-2 human interferon (pIF-2-trp), were grown in LB medium to a density of 1.5–2×10$^8$ cells/ml. These cells were then infected at a multiplicity of 15 with different phage λ lysates, as indicated in Table 3 (below). Cultivation continued with intensive aeration at 25° C. for 13 hr. Control cultures, not infected with phage, were incubated at 37° C. for the same period.

TABLE 3

| | Bacterial Cell Culture | Phage | Interferon (Units/L) |
| --- | --- | --- | --- |
| 1 | K 802-pIF-2-trp Su$^+$ | | 8.0 × 10$^7$ |
| 2 | K 802-pIF-2-trp Su$^+$ | λcI$_{857}$ | 77 × 10$^7$ |
| 3 | K 802-pIF-2-trp Su$^+$ | λcI$_{857}$Q$_{am117}$R$_{am54}$ | 340 × 10$^7$ |
| 4 | K 802-pIF-2-trp Su$^+$ | λ-pIF-2-trp cI$_{857}$Q$_{am117}$R$_{am54}$ | 1400 × 10$^7$ |
| 5 | K 802-pIF-2-trp Su° | λ-pIF-2-trpcI$_{857}$Q$_{am117}$R$_{am54}$ | 3000 × 10$^7$ |

As shown in Table 3, when bacterial cells which were transformed with plasmid containing the targeted gene were infected with phage λ containing only the temperature-sensitive mutation in cI, interferon expression increased by about 10-fold compared to control, non-infected cultures. Adding the amber-mutations in Q and R genes further increased expression by about 40-fold compared to control bacterial cells.

Adding a copy of the interferon gene to phage λ with cI, Q and R mutations increased interferon synthesis by 175-fold over controls. Finally, when a non-suppressing, Su°, strain of *E. coli*, transformed by a plasmid bearing a copy of the interferon gene, was infected with phage λ, also having a copy of the interferon gene, as well as cI, Q and R mutations, the bacterial host cells produced about 375 times more recombinant protein than the control cells transformed by plasmid alone.

EXAMPLE 5

Enhanced Recovery of Biologically Active Recombinant Interferon by Phage-Mediated Host Cell Lysis Strain *E. Coli* SG 20050 was transformed by a plasmid bearing two copies of the human interferon alpha-2b gene (pIF-14) by standard methods. The transformant cells were grown up in 80 liters of LB medium at 37° C. with intensive aeration to a density of 2×10$^8$ cells/ml. The culture was divided into two portions. The first was not infected with phage. The second was infected with phage λ lysate harvested from *E. coli* K 802/λ cI$_{857}$ Q$_{am\ 117}$ R$_{am\ 54}$ at a multiplicity of 10 phage bodies per bacterial cell. The control cells were incubated for 19 hr at 37° C. and the phage-infected cells were incubated for 19 hr at 21° C.

Interferon production in both control and phage-infected cultures was about 20% of the total cellular protein. However, the interferon in control cells was associated at least in part with insoluble inclusion bodies. Thus, it was not possible to determine its biological activity without solubilization, denaturation and renaturation. In contrast, the specific activity of the soluble interferon released into the medium following phage-mediated cell lysis, was readily determined by standard immunoenzyme assay. The interferon activity was 4×10$^{10}$ IU/liter (200 mg/liter).

Pre-clinical toxicological studies of recombinant human alpha-2β interferon produced by the phage super-production method of the present invention showed that the compound was practically non-toxic. Intra-abdominal and intramuscular injections of the recombinant interferon in white mice and Wistar rats at $8.5 \times 10^9$ ME/kg ($2.5 \times 10^5$ times the maximum human dose) and intravenous injections in mice and rabbits at $4.25 \times 10^9$ ME/kg ($1.25 \times 10^5$ times the human therapeutic dose) produced no pronounced intoxication or death of the animals. Four months of injections in Wistar rats at $6 \times 10^5$, $6 \times 10^6$ and $3 \times 10^7$ ME/kg (18, 180 and 900 times the human therapeutic dose, respectively) showed no damage to the main organs and bodily systems of the experimental animals. Likewise, three months of intravenous injections in rabbits of $6 \times 10^5$ and $6 \times 10^6$ ME/kg, and two months of intramuscular injections in dogs at $3 \times 10^6$ ME/kg showed no signs of damage to the organ systems.

During immunotoxic and allergenic analysis of recombinant interferon, the induction of cellular and humoral immunity reactions, as well as delayed and immediate hypersensitivity reactions were studied. The results indicated that no immunotoxic or allergenic influence was produced. The recombinant interferon also had no mutagenic or DNA-damaging effects in bacteria during metabolic activation in vitro or in bone marrow of mouse embryos in vivo.

Embryotoxic studies of recombinant interferon were conducted in pregnant hamadryad baboon females. Daily intramuscular doses during organogenesis ($20^{th}$ to $50^{th}$ days of pregnancy) caused defects in embryo development leading to miscarriage or stillbirth. Similar results were obtained for recombinant interferon analogs, and most probably could be explained by a powerful antiproliferative action of interferons. It is possible that the miscarriage may be attributed to a "cancellation" of immunologic tolerance of maternal organism towards the fetus, caused by immuno-modulating action of the protein.

Recombinant interferon was also studied in Ukrainian clinics. Based on these clinical studies, the recombinant interferon was shown to be useful in the treatment of a variety of human diseases and conditions. For example, recombinant interferon was effective in treating acute and chronic hepatitis B, acute viral, bacterial and mixed infections, acute and chronic septic diseases, herpetic infections, herpes zoster, papillomatosis of larynx, multiple sclerosis, and various cancers, including melanoma, renal cell carcinoma, bladder carcinoma, ovarian carcinoma, breast cancer, Kaposi's sarcoma and myeloma.

The contraindications in human clinical applications were prolonged (several months) use at high doses, allergy and pregnancy. The possible side effects noted were small and transitory "flu-like" symptoms and at prolonged regimens, leuko and trombocytopenia were marked.

While we have described a number of embodiments of this invention, it is A apparent that our description of the invention can be altered to provide other embodiments that utilize the basic process of this invention. Therefore, it will be appreciated by those of skill in the art that the scope of this invention is to be defined by the claims appended hereto rather than the specific embodiments that have been described in detail above by way of example.

What is claimed is:

1. An *E. coli* host cell with a plasmid having at least one copy of an expressible eukaryotic gone encoding a protein, wherein said *E. coli* host cell is lytically infected with bacteriophage λ having $cI_{857}$, $Q_{am117}$, and $R_{am54}$ mutations.

2. The host cell of claim 1, wherein said protein is human alpha-2b interferon.

3. The host cell of claim 1, wherein said *E. coli* host cell lacks a suppressor for repairing amber-mutations.

4. The host cell of claim 1, further comprising recA⁻13.

5. An *E. coli* host cell with a plasmid having at least one copy of an expressible eukaryotic gene encoding a protein, wherein said *E. coli* host cell is lytically infected with bacteriophage λ having $cI_{857}$, $Q_{am117}$, and $R_{am54}$ mutations and at least one copy of an expressible eukaryotic gene encoding said protein.

6. The host cell of claim 5, wherein said *E. coli* host cell lacks a suppressor for repairing amber-mutations.

7. The host cell of claim 4, wherein said protein is human alpha-2b interferon.

8. An *E. coli* host cell with a plasmid having at least one copy of an expressible eukaryotic gene encoding a protein, wherein said *E. coli* host cell is lytically infected with a bacteriophage λ, wherein the bacteriophage λ has at least one mutated gene selected from the group consisting of N, Q and R.

9. The *E. coli* host cell of claim 8, wherein the bacteriophage λ has a temperature-sensitive mutation.

10. The *E. coli* host cell of claim 9, wherein the temperature-sensitive mutation is $cI_{857}$.

11. The *E. coli* host cell of claim 8 which lacks a suppressor for repairing amber-mutations.

12. The *E. coli* host cell of claim 8 which is recA deficient.

13. The host cell of claim 8, wherein said protein is human alpha-2b interferon.

14. An *E. coli* host cell with a plastmid having at least one copy of an expressible heterologous en totic gene encoding a protein, wherein said *E. coli* host cell is lytically infected with bactetophage lambda, wherein the bacteriophage lambda has at least one mutated gene selected from the group consisting of N, Q, and R and at least one copy of an expressible heterologous eukaryotic gene encoding said protein.

15. The host cell of claim 14, wherein said protein is human alpha-2b interferon.

16. The host cell of claim 14, wherein said *E. coli* host cell lacks a suppressor for repairing amber-mutations.

* * * * *

UNITED STATES PATENT AND TRADEMARK OFFICE
CERTIFICATE OF CORRECTION

PATENT NO. : 6,268,178 B1
DATED : July 31, 2001
INVENTOR(S) : V. Kordyum et al.

It is certified that error appears in the above-identified patent and that said Letters Patent is hereby corrected as shown below:

<u>Column 12,</u>
Line 9, "eukaryotic gone" should be changed to -- eukaryotic gene --
Line 46, "plastmid having" should be changed to -- plasmid having --
Line 47, "en totic gene" should be changed to -- eukaryotic gene --

Signed and Sealed this

Thirtieth Day of March, 2004

JON W. DUDAS
*Acting Director of the United States Patent and Trademark Office*